United States Patent [19]
Pond et al.

[11] 3,936,418
[45] Feb. 3, 1976

[54] BENZOTRIAZOLE ORTHO-ESTER ULTRAVIOLET STABILIZERS AND THEIR USE IN ORGANIC COMPOSITIONS

[75] Inventors: David Martin Pond; Richard Hsu-Shien Wang, both of Kingsport, Tenn.

[73] Assignee: Eastman Kodak Company, Rochester, N.Y.

[22] Filed: Oct. 2, 1974

[21] Appl. No.: 511,565

[52] U.S. Cl........ 260/45.8 NT; 106/176; 260/308 B
[51] Int. Cl.²............................................ C08K 5/34
[58] Field of Search.. 260/308 B, 45.8 ST, 45.8 NT; 106/176

[56] References Cited
UNITED STATES PATENTS 3,004,896 10/1961 Heller et al................ 260/45.85 NT
3,366,668 1/1968 Strokel et al................. 260/45.85 T

*Primary Examiner*—V. P. Hoke

[57] ABSTRACT

The invention relates to benzotriazole ortho-ester compounds which have been found to be effective ultraviolet stabilizers. The invention also relates to ultraviolet degradable organic compositions containing a stabilizing amount of the benzotriazole ortho-ester composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

40 Claims, No Drawings

BENZOTRIAZOLE ORTHO-ESTER ULTRAVIOLET STABILIZERS AND THEIR USE IN ORGANIC COMPOSITIONS

This invention relates to benzotriazole ortho-ester ultraviolet stabilizers and their use in organic compositions. More particularly, the invention relates to benzotriazole ortho-ester compositions and the stabilization of ultraviolet degradable organic compositions against deterioration resulting from the exposure to such radiations with such benzotriazole compositions.

The degradative effect of ultraviolet light on various organic compositions is well known in the art. The photo-deterioration or degradation is of particular concern with organic photo-degradable compositions which are exposed to ultraviolet light, such as sunlight, for long periods of time. One group of such photodegradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 and 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing benzotriazole orthoester compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations, including short wavelength visible radiations.

Further objects and advantages of the invention will be apparent to those skilled in the art from the accompanying disclosure and claims.

In accordance with the present invention, benzotriazole orthoester compositions are provided which are useful as ultraviolet stabilizers or ultraviolet screening agents. These organic compositions contain at least one benzotriazole group-containing composition either connected directly or connected through a carboxyl group to an aromatic, heterocyclic or alkyl moiety. The polychromophoric compositions of the present invention have the following structure:

(A)$_x$—C wherein A is a group having the structure

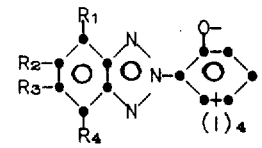

wherein $R_1$, $R_2$, $R_3$ and $R_4$ are hydrogen, lower alkyl or substituted lower alkyl having 1 to 12 carbon atoms, cycloalkyl, substituted cycloalkyl, aryl or substituted aryl having 6 to 18 carbon atoms, lower alkylaryl, arylsubstituted-aryl, chloro, bromo, alkoxy, substituted amino, cyano, carboxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$.

l is a substituent listed above for $R_1$, $R_2$, $R_3$, and $R_4$ and is present on all positions of the benzenoid ring, except the carbon atom attached to the N substituent and the carbon atom attached to the connecting oxygen atom. The connecting oxygen atom is attached to the benzenoid ring ortho to the carbon atom connected to the N substituent. The l substituents can all be one of the substituents listed above or different listed substituents; X is an integer of 1 to 6, preferably 1 to 3;

C is a moiety having the formula:

1.

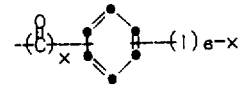

or

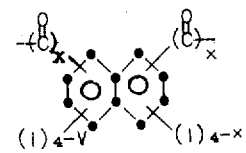

I is the same substituent as listed above and is present in all positions of the benzenoid ring except the carbon atom attached to the carbonyl group connecting the A and C moieties. The A moiety is attached to the benzenoid ring in from 1 to 6 positions. If two A moieties are attached to the C moiety they can be attached in the ortho, meta or para position from each other. If three A moieties are attached to the C moiety they can be attached in the ortho or meta positions from each other. The I substituents can all be one of the substituents listed above or different listed substituents.

X is an integer between 2 and 6 and V is an integer between 1 and 4.

2.

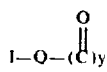

Q is substituted or unsubstituted acyclic, cyclic, or polycyclic aliphatic moiety containing 1 to 18 carbons.

I may be a hydrogen, hydroxy, halogen, cyano, $C_1$–$C_{12}$ substituted or unsubstituted alkyl, amino, alkylamino, dialkylamino, arylamino, diarylamino, alkoxy, aryl or aryloxy group. Y is an integer between 2 and 6.

3.

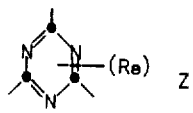

$R_8$ may be hydrogen, hydroxy, halogen, $C_1$–$C_{12}$ substituted or unsubstituted alkyl, amino, alkylamino, dialkylamino, arylamino, diarylamino or unsubstituted alkyl, alkoxy or aryloxy group. Z is an integer 1, 2 or 3.

4.

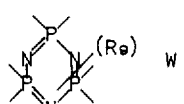

$R_9$ may be a hydrogen, hydroxy, halogen, $C_1$–$C_{12}$ substituted or unsubstituted alkyl, amino, alkylamino, dialkylamino, arylamino, diarylamino, alkoxy, or aryloxy group. W is an integer between 1 and 6.

Suitable heterocyclic A groups having the structure

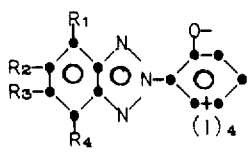

are for example substituted and unsubstituted benzotriazoles such as 2-(5-chloro-2H-benzotriazol-2-yl)phenoxy, 2-(2H-benzotriazol-2-yl)-4-methylphenoxy, 2-(5-methoxy-2H-benzotriazol-2-yl)phenoxy, 2-(2H-benzotriazol-2-yl)-4,6-dimethylphenoxy, 2-(5-chloro-2H-benzotriazol-2-yl)-4-methylphenoxy, 2-(5-chloro-2H-benzotriazol-2-yl)-4,6-dimethylphenoxy, 2-(2H-benzotriazol-2-yl)-4-chlorophenoxy, 2-(2H-benzotriazol-2-yl)-4,6-dichlorophenoxy, 2-(5-methoxy-2H-benzotriazol-2-yl)-4,6-dimethylphenoxy, 2-(5-methoxy-2H-benzotriazol-2-yl)-4-chlorophenoxy, 2-(2H-benzotriazol-2-yl)-4,6-di-tert-amylphenoxy, 2-(2H-benzotriazol-2-yl)-4-isopropylphenoxy, 2-(5-chloro-2H-benzotriazol-2-yl)-4,6-di-tert-amylphenoxy, 2-(5-chloro-2H-benzotriazol-2-yl)-4-isopropylphenoxy, 2-(2H-benzotriazol-2-yl)-4-phenylphenoxy, 2-(5-chloro-2H-benzotriazol-2-yl)-4-phenylphenoxy, 2-(5-methoxy-2H-benzotriazol-2-yl)-4-phenylphenoxy, 2-(5-methoxy-2H-benzotriazol-2-yl)-4,6-di-tert-amylphenoxy, 2-(4,5-dimethyl-2H-benzotriazol-2-yl)-4-methylphenoxy, and the like.

Suitable C moieties having the formula

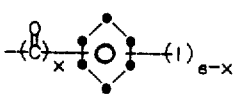

are for example, phthaloyl, isophthaloyl, terephthaloyl, trimellitoyl, hemimellitoyl, mesoyl, pyromellitoyl, 4-chlorophthaloyl, 4-methoxyphthaloxyl, 4-methylphthaloyl, 5-chloroisophthaloyl, 5-methoxyphthaloyl, 5-methylisophthaloyl, 5-phenoxyisophthaloyl, 2-chloroterephthaloyl, 2-methoxyterephthaloyl, 2-methylterephthaloyl, 5-methoxyhemimellitoyl, 5-chlorohemimellitoyl, 3-chloromellitoyl, 3-chloromesoyl, and the like.

Suitable C moieties having the formula

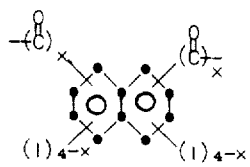

are for example, 1,2-dinaphthoyl, 1,3-dinaphthoyl, 1,4-dinaphthoyl, 1,5-dinaphthoyl, 1,6-dinaphthoyl, 1,7-dinaphthoyl, 1,8-dinaphthoyl, 2,6-dinaphthoyl, 2,7-dinaphthoyl, 2,8-dinaphthoyl, 5-methoxy-1,2-dinaphthoyl, 5-chloro-1,2-dinaphthoyl, 6-methoxy-1,3-dinaphthoyl, 4-chloro-1,8-dinaphthoyl, 6,7-dimethyl-1,4-dinaphthoyl, 8-methoxy-1,3-dinaphthoyl, 1,2,5,6-tetranaphthoyl, 1,4,5,8,-tetranaphthoyl, 2,4,6-trinaphthoyl, 1,3,5-trinaphthoyl, and the like.

Suitable C moieties having the formula

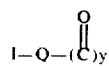

are for example, malonoyl, succinyl, adipoyl, 1,12-didodecoyl, 1,2-dicarbonylcyclohexane, 1,4-dicarbonylcyclohexane, 1,3-dicarbonylcyclopentane, camphoroyl, 2,2-dimethylmalonoyl, 2,3-dimethylsuccinyl, and the like.

Suitable C moieties having the formula

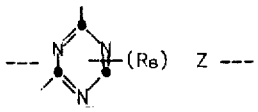

are for example s-triazinyl, phenoxy-s-triazinyl, chloro-s-triazinyl, methoxy-s-triazinyl, and the like.

Suitable C moieties having the formula

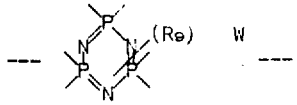

are for example cyclotriphosphazenyl, phenoxycyclotriphosphazenyl, 1,3-diphenoxycyclotriphosphazenyl, 1,3,5-triphenoxycyclotriphosphozenyl, chlorocyclotriphosphazenyl, 1,3-dichlorocyclotriphosphazenyl, 1,3,5-trichlorocyclotriphosphazenyl, 1,1-ethylenedioxycyclotriphosphazenyl, 1,1-(o-phenylenedioxy)cyclotriphosphazenyl, and the like.

The ortho-benzotriazole ester ultraviolet stabilizer of the present invention can be prepared by reacting the acid chloride with the hydroxy moiety on the benzotriazole. One group of organic compounds useful as ultraviolet stabilizers is, for example,

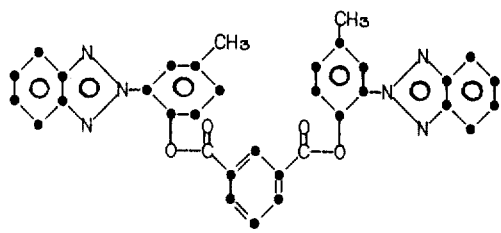

One method for preparing these compounds is according to the following procedure:

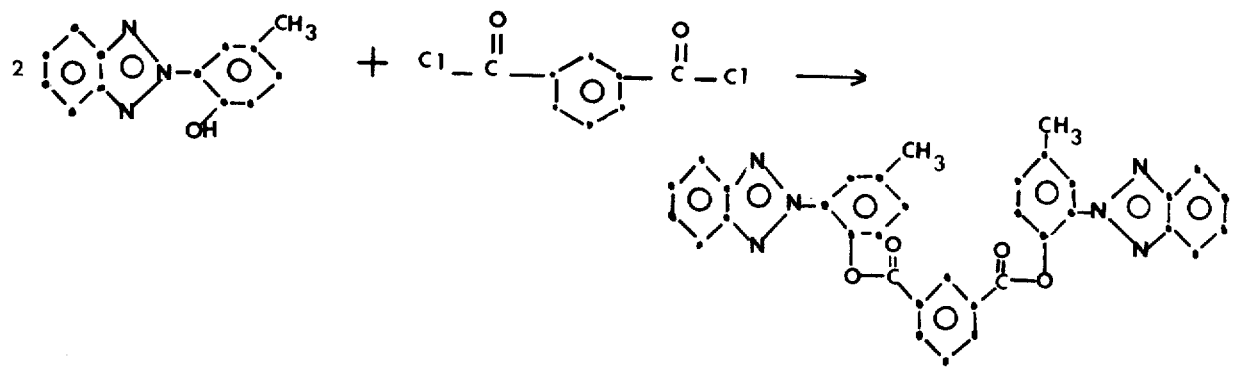

The acid chlorides can be prepared by reaction of the corresponding acid [See Zh. Obshch. Khim., 38, 100 1-5 (1968); Chem. Abstr. 69, 96568 (1968)] with freshly distilled thionyl chloride [See J. Chem. Soc. 101, 2476 (1912)].

s-Triazine esters constitute a group of organic compounds useful as ultraviolet stabilizers, for example:

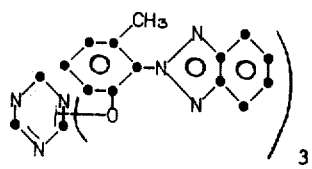

These are prepared by the following procedure:

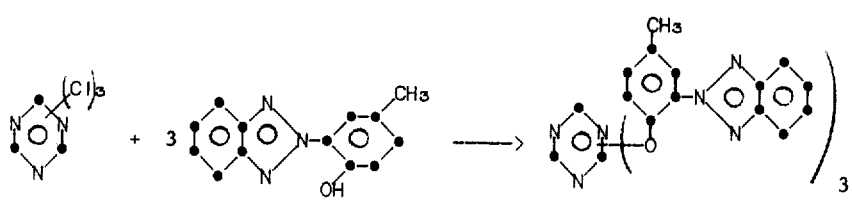

Cyanuric chloride

Cyanuric chloride is commercially available or can easily be prepared via the trimerization of cyanogen chloride [see Brit. 602,816 (1948) or U.S. 2,416,656 (1947)].

Another group of useful organic ultraviolet stabilizers is the cyclotriphosphazenes. For example,

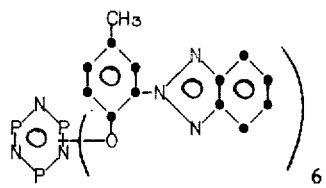

One method for preparing these compounds is according to the following procedure

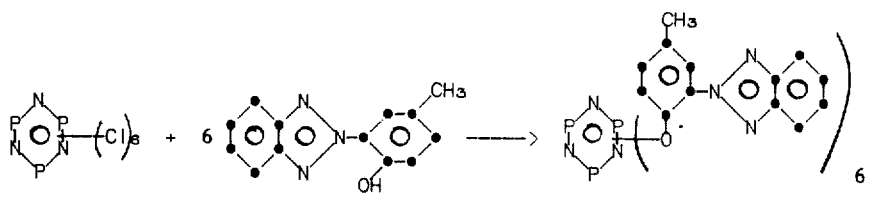

The hexachlorocyclotriphosphazene is commercially available as can easily be made in the reaction of ammonium chloride and phosphorus pentachloride [see J. Chem. Soc., A, F68 (1971)].

The phenols were obtained from commercial sources, or were prepared by standard methods.

The heterocyclic compositions can be added to organic compositions which are susceptible to ultraviolet degradation. Such compositions include, for example, polymeric compositions such as polyester fiber and molding compositions, such as polyethylene terephthalate, polymethylene terephthalate and the like; polyolefins such as, for example, high, medium and low density polyethylene, polypropylene, polybutene and the like; polyamides such as N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The benzotriazole ortho-ester compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate and polymethylene terephthalate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel benzotriazole ortho-ester ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1

Preparation of bis[o-(2H-benzotriazol-2-yl)-4-methylphenyl] isophthalate (1) can be prepared by the following procedure:

o-Nitroaniline (0.5 mole) was diazotized in the usual manner with concentrated hydrochloric acid (200 ml.) and sodium nitrite (0.5 mole). The clear diazonium solution was added slowly to a cold solution (0°–5°) of p-cresol (0.5 mole) in 450 ml of 10% sodium hydroxide. The mixture was stirred for 1 hour and 2-nitro-2'-hydroxy-5'-methylazoaniline (A) was filtered out (60% yield). One-tenth mole of A was dissolved in 100 ml. of 2N NaOH. Zinc dust (30 g.) and sodium hydroxide (50 ml. of a 25% solution) were added slowly to the well-stirred solution to keep the temperature below 45°C. The mixture was then cooled to <30°C. and acidified with concentrated hydrochloric acid. After stirring for 2 hours, the precipitate was filtered and recrystallized from toluene (mp 122-24°) to give o-[2H-benzotriazol-2-yl)-4-methylphenol (B). A solution containing 9.0 g. (0.04 mole) of B and 4.0 6 gm. (0.02 mole) of isophthaloyl chloride in 200 ml. of pyridine was heated with stirring at 50°–60° for 15 hrs. The reaction mixture was poured into cold dilute hydrochloric acid and a solid precipitated. The solid was filtered, and air-dried to give 1 as a white solid (30%, mp. 115°–8°).

EXAMPLE 2

Preparation of bis[o-(2H-benzotriazol-2-yl)-4-methylphenyl]terephthalate 2 can be carried out in the same manner as Example 1. Thus, B was reacted with terephthaloyl chloride in pyridine to give 2 in 50%yield.

EXAMPLE 3

Tris[o-(2H-benzotriazol-2-yl)-4-methylphenyl] trimellitate (3) can be prepared in a similar manner by reaction of B with 1,2,4-benzenetricarboxylic acid chloride.

EXAMPLE 4

Bis[o-(2H-benzotriazol-2-yl)-4-methylphenyl]adipate (4) was prepared by reacting B with adipoylchloride in refluxing p-xylene (95%, mp. 145°–48°).

EXAMPLE 5

Bis[o-(2H-benzotriazol-2-yl)-4-methylphenyl] dodecanoate (5) was prepared in a similar manner by reacting B (Example 1) with 1,12-dodecanoylchloride in refluxing p-xylene (65%).

EXAMPLE 6

2,4,6-Tris[o-(2H-benzotriazol-2-yl)-4-methylphenyl]-s-triazine (6) was prepared by condensing B (Example 1) with cyanuric chloride in the presence of sodium hydroxide in aqueous acetone held at 60° for 15 hr. Compound 6 was obtained as an off-white solid (86%, mp. 158°–161°).

EXAMPLE 7

2-Phenoxy-4,6-bis[o-(2H-benzotriazol-2-yl)-4-methylphenyl]-s-triazine (7) was prepared in the following manner.

2,4-Dichloro-6-phenoxy-s-triazine (C) was prepared in 45% yield via the condensation of one equivalent of phenol with cyanuric chloride in chloroform at 50° which also contained one equivalent of sodium hydroxide. The product C, obtained as a white crystalline solid (mp. 110°–112°), was condensed in a second step with B in a manner similar to that described in Example 6. During the course of the reaction a solid appeared which was filtered, air-dried and identified as 7.

EXAMPLE 8

Hexakis[o-(2H-benzotriazol-2-yl)-4-methylphenyl]-cyclotriphosphazene (8) was prepared in low yield (30%) by refluxing B with hexachlorocyclotriphosphazene and KHCO₃ in 2-butanone for 50 hr. The product 8 was obtained as an insoluble, off-white solid.

EXAMPLE 9

A dry mixture of the stabilizer and granulated poly(tetramethylene terephthalate) was extruded into 1/16-inch diameter rods, pelletized and injection molded into 2½- × ½- × 1/16-inch flat bars; these flat bars were exposed to a 280–700 nm. mercury lamp. The ultraviolet stabilization provided by the heterocyclic stabilizers of the present invention is shown in Table 1.

TABLE 1

Effectiveness of Ultraviolet Stabilizers
In Poly(tetramethylene terephthalate)

| Compound (0.5%) | FWIS (Flatwise Impact Strength) | | |
|---|---|---|---|
| | Initial | 300 Hr. | 500 Hr. |
| None | 20 | 3 | 1 |
| 1 | 19 | 19 | 17 |
| 2 | 18 | 17 | 16 |
| 3 | 19 | 18 | 18 |
| 4 | 17 | 17 | 15 |
| 5 | 18 | 16 | 15 |
| 6 | 19 | 19 | 17 |
| 7 | 20 | 19 | 16 |
| 8 | 19 | 18 | 18 |

These benzotriazole ortho-ester compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:

1. An organic composition susceptible to ultraviolet degradation stabilized against such degradation with a stabilizing amount of a composition of matter comprising polychromophoric compounds having the formula:

(A)$_x$—C wherein A is a group having the structure

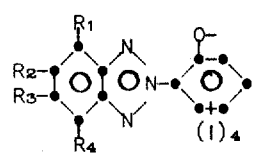

wherein $R_1$, $R_2$, $R_3$ and $R_4$ are hydrogen, chloro, bromo, lower alkyl, substituted lower alkyl, cycloalkyl, substituted cycloalkyl, aryl, substituted aryl, lower alkyl-aryl, aryl-substituted-aryl, alkoxy, substituted amino, cyano, carboxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;

I is the same as $R_1$, $R_2$, $R_3$ and $R_4$ and is present on all positions of the benzenoid ring, except the carbon atom attached to the heterocyclic ring and the carbon atom attached to the carbonyl group connecting the heterocyclic aromatic A group with the aromatic C group, $a$ is an integer of 2 to 6

$x$ is an integer of 1 to 6; and

C is one of the following:

1. An aromatic group having the formula:

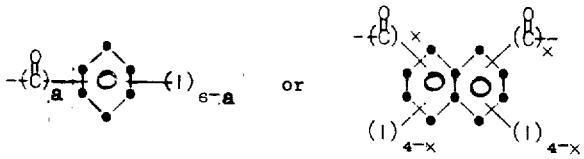

wherein I is the same substituent as listed above and is present in all positions of the benzenoid ring except the carbon atom attached to the carbonyl group connecting the A and C moieties, and said I substituents can all be one of the substituents listed above or different listed substituents; or 2. An aliphatic group having the formula

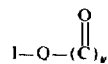

wherein Q is substituted or unsubstituted acyclic, cyclic or polycyclic aliphatic moiety containing 1 to 18 carbons.

I may be a hydrogen, hydroxy, halogen, cyano, $C_1$-$C_{12}$ substituted or unsubstituted alkyl, amino, alkylamino, dialkylamino, arylamino, diarylamino, alkoxy, aryl or aryloxy group; y is an integer between 2 and 6.

2. A composition of matter according to claim 1 having the formula:

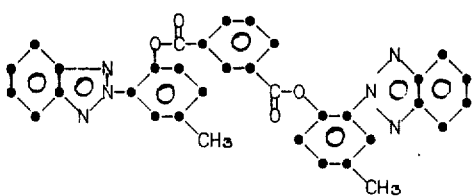

3. An organic composition according to claim 1 containing a stabilizing amount of a composition of matter having the formula:

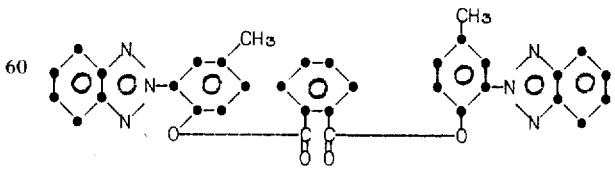

4. An organic composition according to claim 1 containing a stabilizing amount of a composition of matter having the formula:

3,936,418

5. An organic composition according to claim 1 containing a stabilizing amount of a composition of matter having the formula:

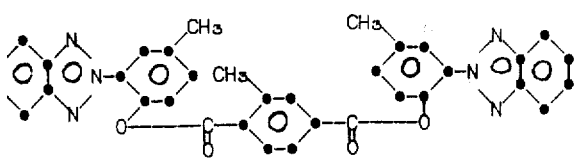

6. An organic composition according to claim 1 containing a stabilizing amount of a composition of matter having the formula:

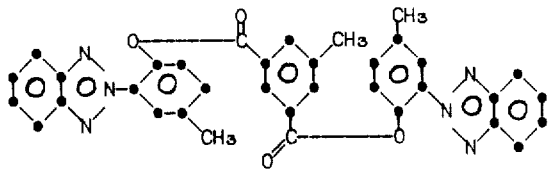

7. An organic composition according to claim 1 containing a stabilizing amount of a composition of matter having the formula:

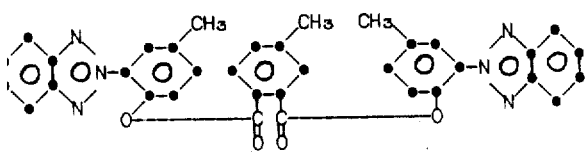

8. An organic composition according to claim 1 containing a stabilizing amount of a composition of matter having the formula:

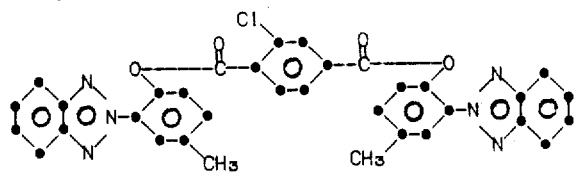

9. An organic composition according to claim 1 containing a stabilizing amount of a composition of matter having the formula:

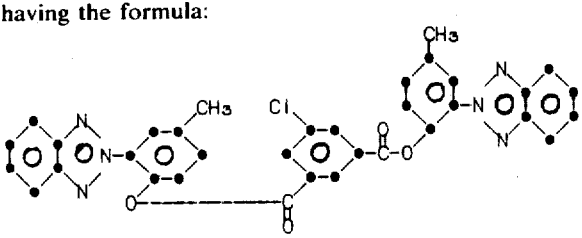

10. An organic composition according to claim 1 containing a stabilizing amount of a composition of matter having the formula:

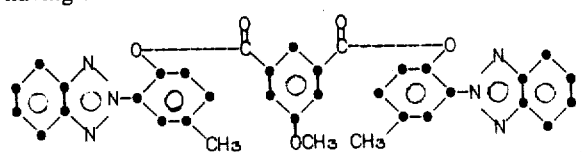

11. An organic composition according to claim 1 containing a stabilizing amount of a composition of matter having the formula:

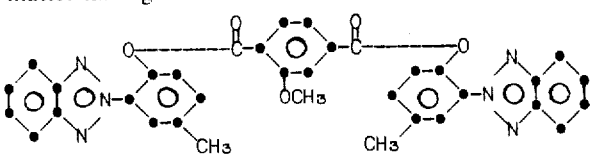

12. An organic composition according to claim 1 containing a stabilizing amount of a composition of matter having the formula:

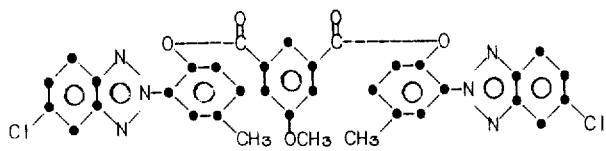

13. An organic composition according to claim 1 containing a stabilizing amount of a composition of matter having the formula:

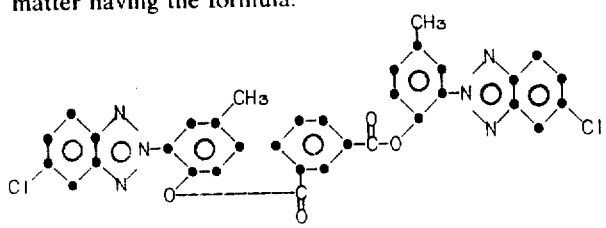

14. An organic composition according to claim 1 containing a stabilizing amount of a composition of matter having the formula:

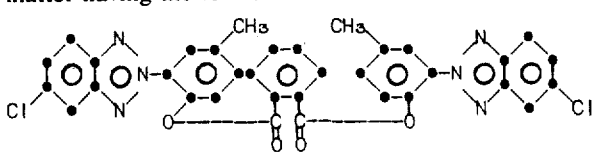

15. An organic composition according to claim 1 containing a stabilizing amount of a composition of matter having the formula:

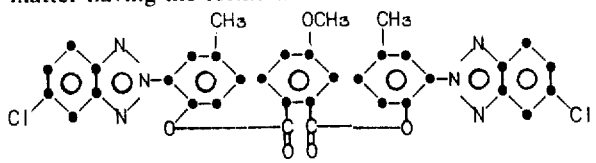

16. An organic composition according to claim 1 containing a stabilizing amount of a composition of matter having the formula:

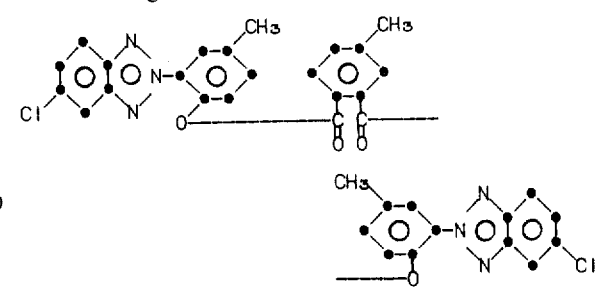

17. An organic composition according to claim 1 containing a stabilizing amount of a composition of matter having the formula:

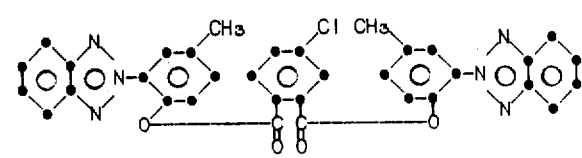

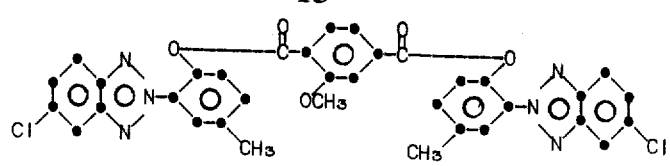

18. An organic composition according to claim 1 containing a stabilizing amount of a composition of matter having the formula:

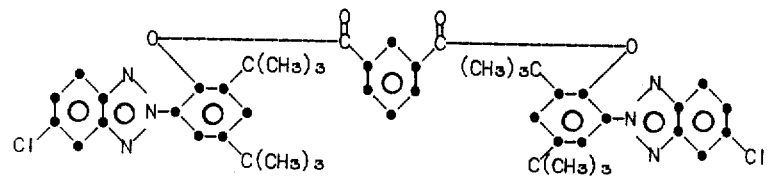

19. An organic composition according to claim 1 containing a stabilizing amount of a composition of matter having the formula:

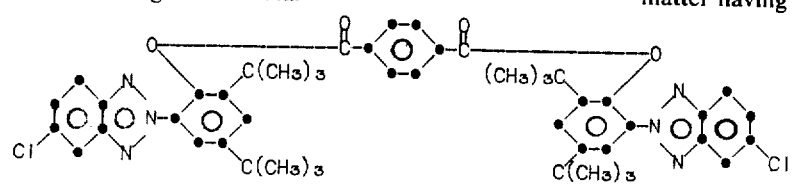

20. An organic composition according to claim 1 containing a stabilizing amount of a composition of matter having the formula:

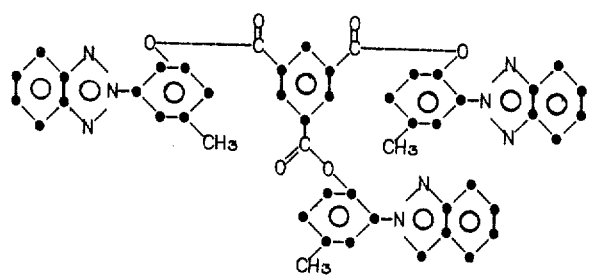

21. An organic composition according to claim 1 containing a stabilizing amount of a composition of matter having the formula:

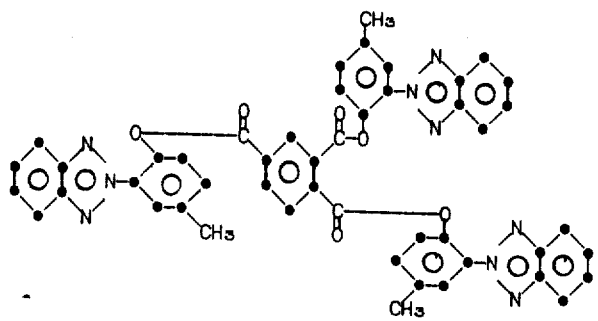

22. An organic composition according to claim 1 containing a stabilizing amount of a composition of matter having the formula:

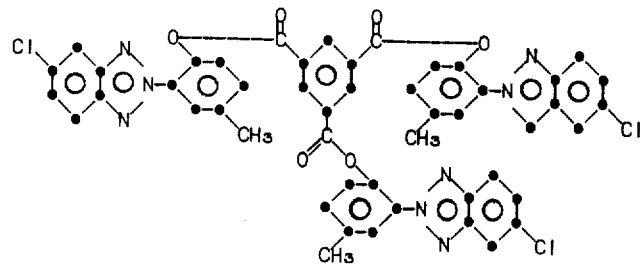

23. An organic composition according to claim 1 containing a stabilizing amount of a composition of matter having the formula:

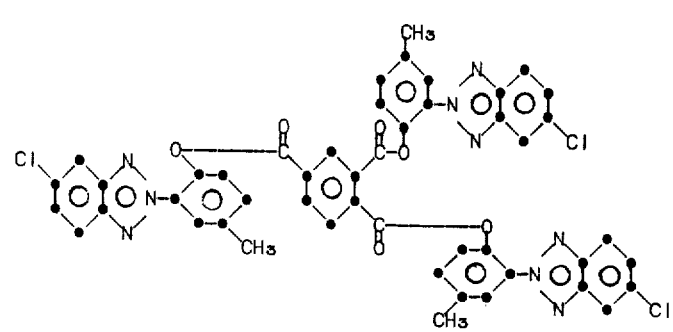

24. An organic composition according to claim 1 containing a stabilizing amount of a composition of matter having the formula:

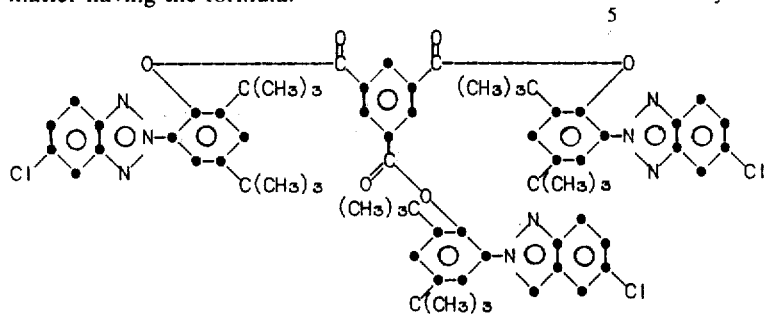

25. An organic composition according to claim 1 containing a stabilizing amount of a composition of matter having the formula:

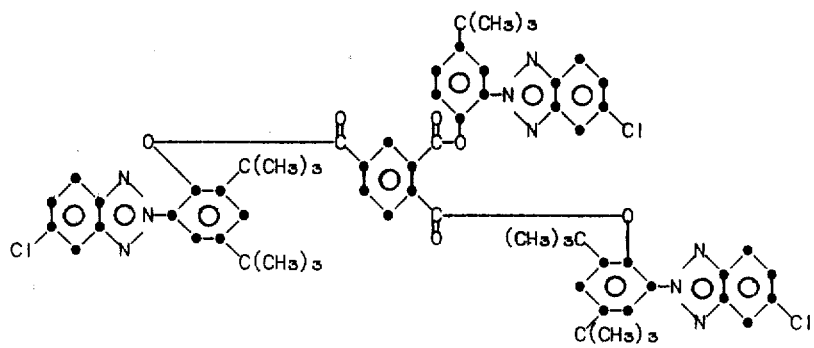

26. An organic composition according to claim 1 containing a stabilizing amount of a composition of matter having the formula:

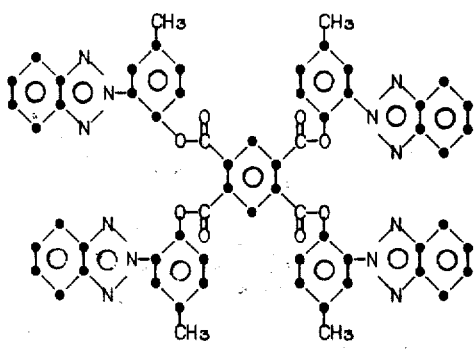

27. An organic composition susceptible to ultraviolet degradation stabilized against such degradation with a stabilizing amount of a composition of matter according to claim 1 having the formula:

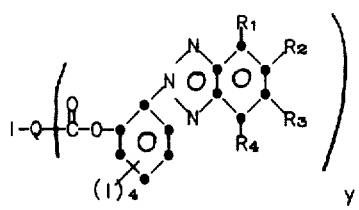

wherein Q is substituted or unsubstituted acyclic, cyclic or polycyclic aliphatic moiety containing 1 to 18 carbons. y is an integer between 2 and 6. $R_1$, $R_2$, $R_3$ and $R_4$ are hydrogen, chloro, bromo, lower alkyl, substituted lower alkyl, cycloalkyl, substituted cycloalkyl, aryl, substituted aryl, lower alkylaryl, alkoxy, amino, substituted amino, cyano, carboxy and the substituents $R_1$ and $R_2$, $R_2$ and $R_3$, $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$; I is the same as $R_1$, $R_2$, $R_3$ and $R_4$ and is present on all positions of the benzenoid ring, except the carbon atom attached to the carbonyl linking substituent, said I substituents can all be one of the substituents listed above or different listed substituents.

28. An organic composition according to claim 27 containing a stabilizing amount of a composition of matter having the formula:

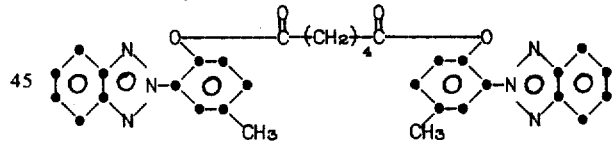

29. An organic composition according to claim 27 containing a stabilizing amount of a composition of matter having the formula:

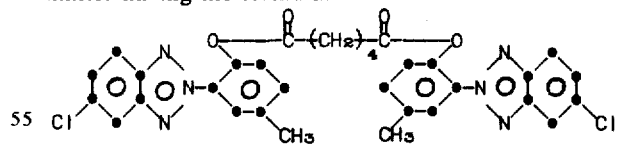

30. An organic composition according to claim 27 containing a stabilizing amount of a composition of matter having the formula:

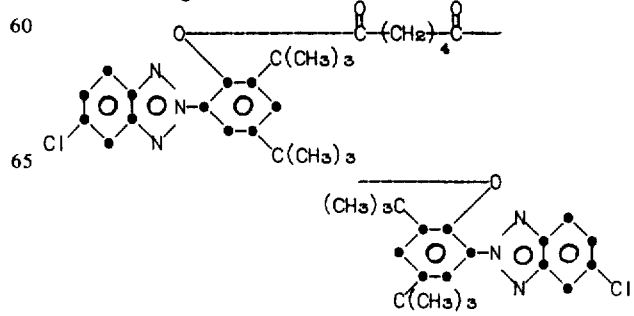

31. An organic composition according to claim 27 containing a stabilizing amount of a composition of matter having the formula:

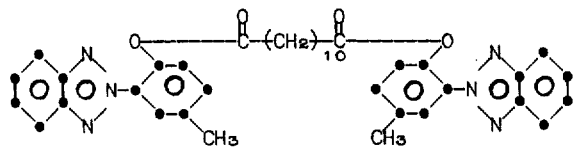

32. An organic composition according to claim 27 containing a stabilizing amount of a composition of matter having the formula:

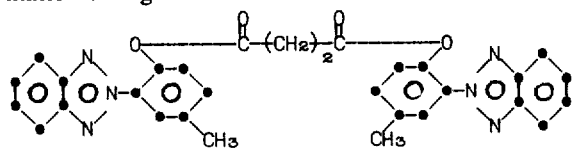

33. An organic composition according to claim 27 containing a stabilizing amount of a composition of matter having the formula:

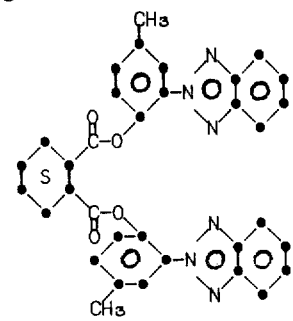

34. An organic composition according to claim 27 containing a stabilizing amount of a composition of matter having the formula:

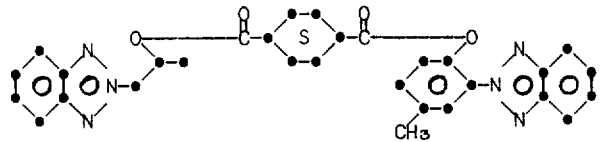

35. An organic composition according to claim 27 containing a stabilizing amount of a composition of matter having the formula:

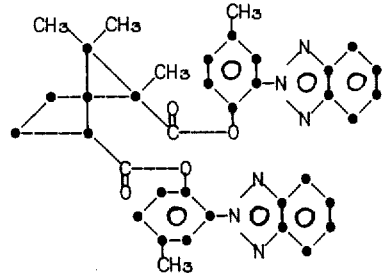

36. An organic composition susceptible to ultraviolet degradation stabilized against such degradation with a stabilizing amount of a composition of matter according to claim 1 having the following formula:

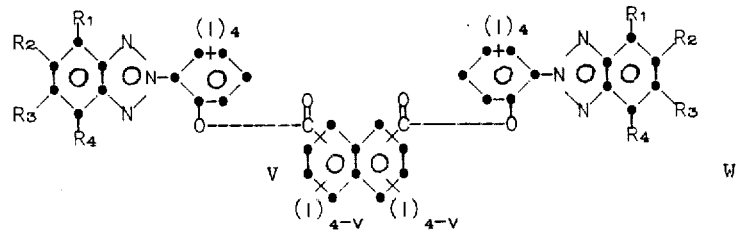

wherein V and W are an integer of 1 to 4;

$R_1$, $R_2$, $R_3$ and $R_4$ are hydrogen, chloro, bromo, lower alkyl, substituted lower alkyl, cycloalkyl, substituted cycloalkyl, aryl, substituted aryl, lower alkylaryl, alkoxy, amino, substituted amino, cyano, carboxy and the substituents $R_1$ and $R_2$, $R_2$ and $R_3$, $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;

I is the same as $R_1$, $R_2$, $R_3$ and $R_4$ and is present on all positions of the benzenoid ring, except the carbon atom attached to the carbonyl linking substituent, said I substituents can all be one of the substituents listed above or different listed substituents.

37. An organic composition according to claim 36 containing a stabilizing amount of a composition of matter having the following formula:

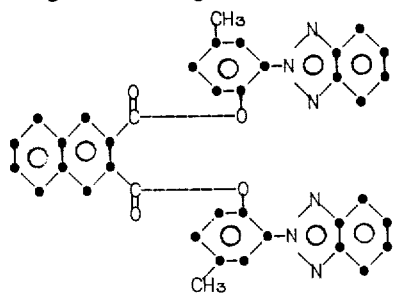

38. An organic composition according to claim 36 containing a stabilizing amount of a composition of matter having the formula:

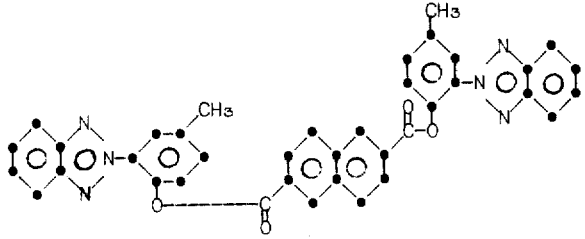

39. An organic composition according to claim 36 containing a stabilizing amount of a composition of matter having the formula:

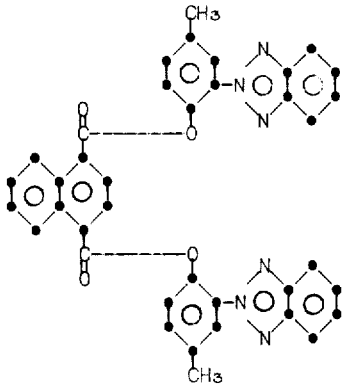

40. An organic composition susceptible to ultraviolet degradation stabilized against such degradation with a stabilizing amount of a composition of matter having the formula:
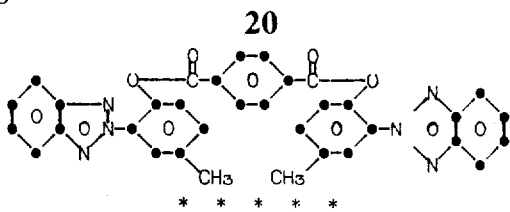
* * * * *

UNITED STATES PATENT OFFICE
CERTIFICATE OF CORRECTION

Patent No. 3,936,418                              Dated February 3, 1976

Inventor(s) David M. Pond and Richard H. S. Wang

It is certified that error appears in the above-identified patent and that said Letters Patent are hereby corrected as shown below:

Column 4, lines 43-48, delete the formula appearing therein and
    insert in place thereof:

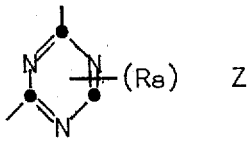   Z

Column 4, lines 52-57, delete the formula appearing therein and
    insert in place thereof:

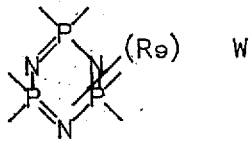   W

Signed and Sealed this eighteenth Day of May 1976

[SEAL]

Attest:

RUTH C. MASON
Attesting Officer

C. MARSHALL DANN
Commissioner of Patents and Trademarks